United States Patent
Chiba

(10) Patent No.: US 8,602,989 B2
(45) Date of Patent: Dec. 10, 2013

(54) CAPSULE MEDICAL APPARATUS SYSTEM

(75) Inventor: Atsushi Chiba, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 103 days.

(21) Appl. No.: 13/070,788

(22) Filed: Mar. 24, 2011

(65) Prior Publication Data

US 2011/0263951 A1 Oct. 27, 2011

Related U.S. Application Data

(63) Continuation of application No. PCT/JP2010/062549, filed on Jul. 26, 2010.

(30) Foreign Application Priority Data

Nov. 19, 2009 (JP) ................................. 2009-264302

(51) Int. Cl.
   *A61B 5/07* (2006.01)
(52) U.S. Cl.
   USPC ........................................................ 600/302
(58) Field of Classification Search
   USPC ........................................................ 600/302
   See application file for complete search history.

(56) References Cited

U.S. PATENT DOCUMENTS

| | | |
|---|---|---|
| 2007/0221233 A1 | 9/2007 | Kawano et al. |
| 2009/0171146 A1 | 7/2009 | Fujita |
| 2009/0227864 A1 | 9/2009 | Sato et al. |
| 2009/0292174 A1 | 11/2009 | Shigemori |

FOREIGN PATENT DOCUMENTS

| | | |
|---|---|---|
| EP | 2 110 067 A1 | 10/2009 |
| JP | SHO 55-089403 | 6/1980 |
| JP | SHO 63-068135 | 3/1988 |
| JP | 2002-051999 | 2/2002 |
| JP | 2004-180860 | 7/2004 |
| JP | 2005-110943 | 4/2005 |
| JP | 2005-312688 | 11/2005 |
| JP | 2009-213613 | 9/2009 |
| WO | WO 2007/077922 A1 | 7/2007 |
| WO | WO 2008/032713 A1 | 3/2008 |
| WO | WO 2008/096744 A1 | 8/2008 |

OTHER PUBLICATIONS

European Search Report dated May 4, 2012 from corresponding European Patent Application No. EP 10 83 1366.9.

*Primary Examiner* — Navin Natnithithadha
*Assistant Examiner* — Etsub Berhanu
(74) *Attorney, Agent, or Firm* — Scully, Scott, Murphy & Presser, P.C.

(57) ABSTRACT

A capsule medical apparatus system includes: a table for placing a subject thereon along a longitudinal direction; an antenna, which is arranged on a body surface of the subject, for receiving in-vivo information transmitted from a capsule medical apparatus inserted in the subject; a cable for transmitting the in-vivo information received by the antenna; a processing device, which is fixed to a longitudinal end portion of the table, for processing the in-vivo information transmitted via the cable; a rotation mechanism for rotating a connecting portion, at which the cable is connected to the processing device, about a rotation axis lying in the longitudinal direction of the table depending on posture change of the subject.

4 Claims, 5 Drawing Sheets

CAPSULE MEDICAL APPARATUS SYSTEM

CROSS-REFERENCE TO RELATED APPLICATIONS

This application is a continuation of PCT international application Ser. No. PCT/JP2010/062549 filed on Jul. 26, 2010 which designates the United States, incorporated herein by reference, and which claims the benefit of priority from Japanese Patent Applications No. 2009-264302, filed on Nov. 19, 2009, incorporated herein by reference.

BACKGROUND OF THE INVENTION

1. Field of the Invention

The present invention relates to a capsule medical apparatus system for acquiring in-vivo information by inserting a capsule medical apparatus into a subject.

2. Description of the Related Art

In recent years, a capsule endoscope system that inserts a capsule medical apparatus into a subject to capture in-vivo images, receives the captured in-vivo images with a receiving device, and displays a group of the in-vivo images received by the receiving device on an image display device has been proposed (see WO/07/077922). With this capsule endoscope system, a doctor observes the in-vivo images displayed on the image display device to perform in-vivo examination.

SUMMARY OF THE INVENTION

A capsule medical apparatus system according to an aspect of the present invention includes: a table for placing a subject thereon along a longitudinal direction; an antenna for receiving in-vivo information transmitted from a capsule medical apparatus inserted into the subject, the antenna being arranged on a body surface of the subject; a cable for transmitting the in-vivo information received by the antenna; a processing device for processing the in-vivo information transmitted via the cable, the processing device being fixed to a longitudinal end portion of the table; and a rotation mechanism for rotating a connecting portion, at which the cable is connected to the processing device, about a rotation axis lying in the longitudinal direction of the table depending on posture change of the subject.

A capsule medical apparatus system according to another aspect of the present invention includes: a table for placing a subject thereon along a longitudinal direction; an antenna for receiving in-vivo information transmitted from a capsule medical apparatus inserted into the subject, the antenna being arranged on a body surface of the subject; a cable for transmitting the in-vivo information received by the antenna; a processing device for processing the in-vivo information transmitted via the cable, the processing device being fixed to a longitudinal end portion of the table; and a rotation mechanism for rotating the processing device about a rotation axis lying in the longitudinal direction of the table depending on posture change of the subject.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Capsule medical apparatus systems according to preferred embodiments of the present invention are described in detail below with reference to the drawings. Note that the present invention is not limited to the embodiments.

Overall Configuration of Capsule Endoscope System

Figure 1:
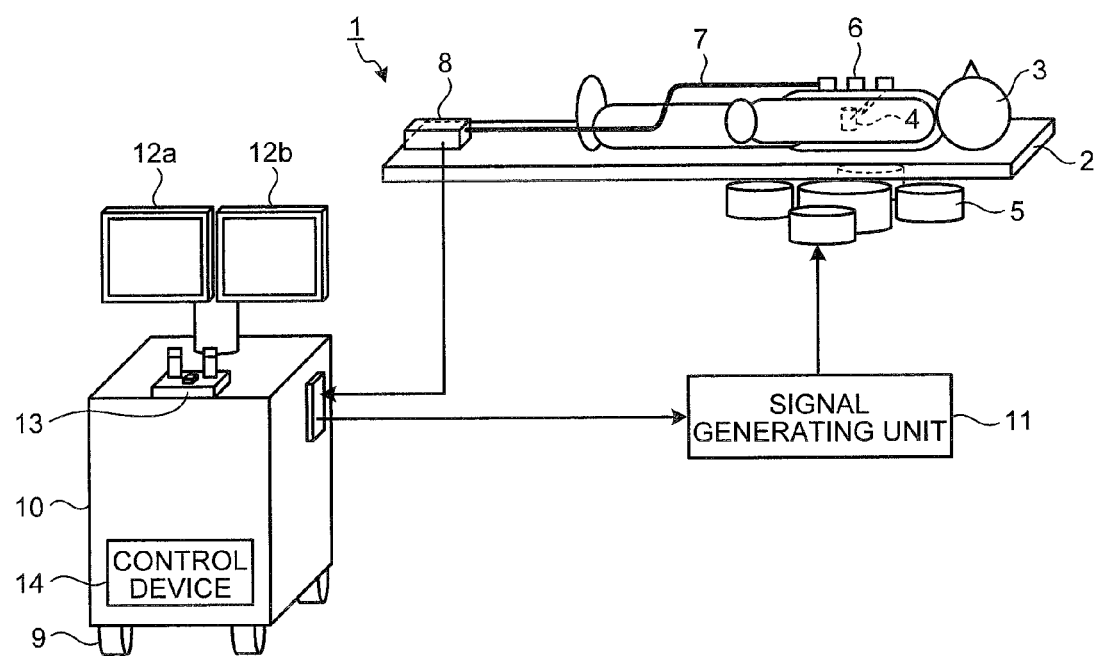
FIG. 1 is a schematic diagram illustrating a configuration of a capsule endoscope system according to an embodiment of the present invention.
Figure 2:
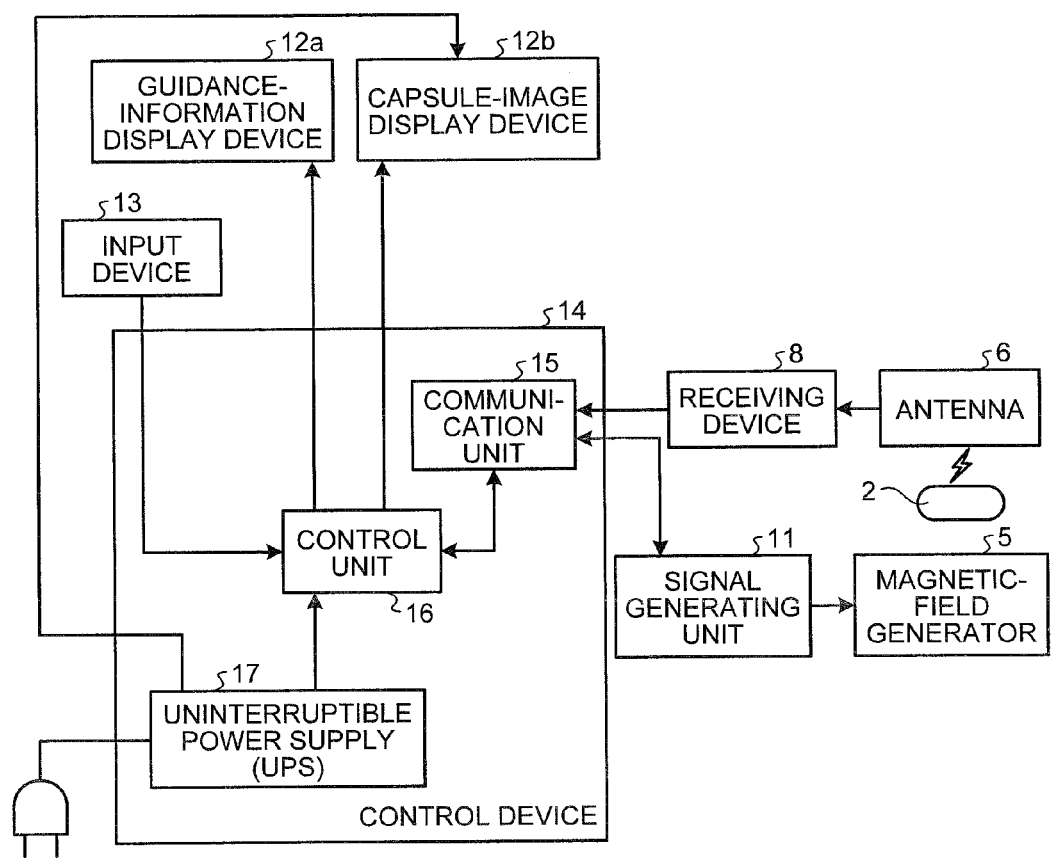
FIG. 2 is a block diagram illustrating an internal configuration of a control device illustrated in FIG. 1.

An overall configuration of a capsule endoscope system according to an embodiment of the present invention is described with reference to FIG. 1 and FIG. 2 first. FIG. 1 is a schematic diagram illustrating a configuration of the capsule endoscope system according to the embodiment of the present invention. FIG. 2 is a block diagram illustrating an internal configuration of a control device illustrated in FIG. 1.

As illustrated in FIG. 1, a capsule endoscope system 1 according to an embodiment of the present invention includes a bed 2 as a table, a capsule endoscope 4 as a capsule medical apparatus, inserted together with liquid, such as water or physiological saline, into a subject 3 placed on the bed 2 to capture an in-vivo image of the subject 3, and a magnetic-field generator 5 for controlling at least one of a position and a posture of the capsule endoscope 4 floating in the liquid. The capsule endoscope system 1 further includes an antenna 6 arranged on a body surface of the subject 3 to receive in-vivo image data of the subject 3 transmitted from the capsule endoscope 4, an antenna cable 7 for transmitting the image data received by the antenna 6, a receiving device 8 for receiving the image data transmitted via the antenna cable 7, and a trolley 10 configured to be movable by including wheels 9.

The capsule endoscope 4 has a capturing function for capturing in-vivo images of the subject 3 and a wireless communication function for wirelessly transmitting various information, such as captured images. The capsule endoscope 4 is formed to have a size easily inserted into the subject 3 and a specific gravity approximately equal to or smaller than a specific gravity of the liquid, such as water or physiological saline. The capsule endoscope 4 moves inside the subject 3 in a helical motion or the like and sequentially captures in-vivo images of the subject 3 at predetermined time intervals, such as once every 0.5 second. The capsule endoscope 4 transmits the captured images wirelessly.

The magnetic-field generator 5 controls at least one of the position and the posture of the capsule endoscope 4 in the subject 3. More specifically, the magnetic-field generator 5 generates and applies a magnetic field on the capsule endoscope 4 inserted into the subject 3 and controls movement of the capsule endoscope 4 in the liquid by magnetic force caused by the magnetic field. The magnetic-field generator 5 thus controls the movement of the capsule endoscope 4, thereby controlling at least one of the position and the posture of the capsule endoscope 4 in the subject 3. With regard to this situation, the capsule endoscope 4 incorporates a magnet for causing a casing to move responsive to the magnetic field generated by the magnetic-field generator 5. Operations of the magnetic-field generator 5 is controlled by a signal generating unit 11 that operates according to a control signal from a control device 14.

The antenna 6, embodied by using a loop antenna, is arranged at a predetermined position on the body surface of the subject 3. The number of the antenna 6 to be arranged is not limited to one, and can be two or more. The receiving device 8 receives the captured image data wirelessly transmitted from the capsule endoscope 4 via the antenna 6 and the antenna cable 7 and outputs the received captured image data to the control device 14.

A guidance-information display device 12a for displaying movement information about the capsule endoscope 4 as guidance information, a capsule-image display device 12b for displaying an image captured by the capsule endoscope 4, and an input device 13, such as a keyboard, a mouse pointer, or a joystick, are provided on a top surface of the trolley 10. The control device 14 is provided inside the trolley 10. As illustrated in FIG. 2, the control device 14 includes a communication unit 15, a control unit 16, and an uninterruptible power supply 17.

The communication unit 15 displays the captured image data received by the receiving device 8 on the capsule-image display device 12b according to a control signal fed from a control unit 16. Meanwhile, the communication unit 15 can output the captured image data to the control unit 16 via a bus line, such as a USB; alternatively, the communication unit 15 can transmit the captured image data to the control unit 16 by using an optical communications system.

The control unit 16 represents a display function of displaying the captured image data received by the receiving device 8 on the capsule-image display device 12b, an image generating function, an image processing function, an image storing function, a subject-data input function, a posture-information display function, a capturing function, a function of outputting a control signal for drive control of the capsule endoscope 4 to the signal generating unit 11, a function of estimating and displaying the position and the posture of the capsule endoscope 4, and the like. The control unit 16 also controls outputs to the guidance-information display device 12a.

The uninterruptible power supply 17 has a function of preventing loss of incoming electric power in the event of power failure to particularly prevent loss of the captured image data received by the receiving device 8. The uninterruptible power supply 17 has a function of, when power failure or wire breakage is detected, outputting a detection signal to the control device 14 to cause the capsule-image display device 12b to display a message prompting shutdown. Such a function allows a healthcare personnel to select an operation to be taken subsequently based on a cause of the power failure. More specifically, when the cause is not so severe as to terminate examination, the healthcare personnel can turn electric power back on to resume the examination, whereas when there are no prospects for recovery, the healthcare personnel can terminate the examination. The uninterruptible power supply 17 can automatically perform a process for terminating examination depending on a period of time elapsed from the power failure.

Figure 3:
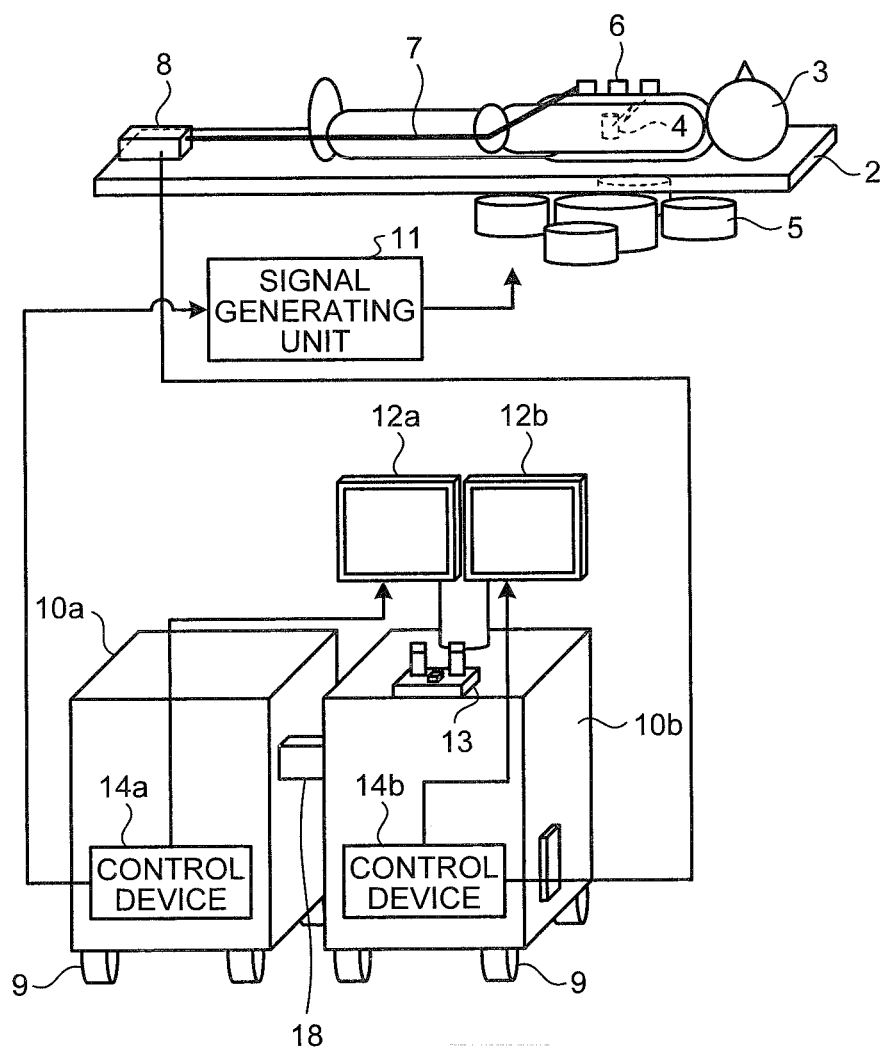
FIG. 3 is a schematic diagram illustrating a configuration of a modification of the capsule endoscope system illustrated in FIG. 1.

In the present embodiment, the number of the trolley 10 is only one; however, alternatively, the trolley 10 can include two trolleys as illustrated in FIG. 3, a trolley 10a and a trolley 10b, and the control device 14 can be divided into two control devices, a control devices 14a and 14b, on a function-by-function basis (e.g., for a guidance-information display function and a capsule-image display function). Note that, with such a configuration, allocating the guidance-information display device 12a and the capsule-image display device 12b individually to the different trolleys can decrease usability; accordingly, the guidance-information display device 12a and the capsule-image display device 12b are desirably positioned on a top surface of the single trolley 10b. This configuration also requires a cable for connecting between the trolley 10a and the trolley 10b; accordingly, to prevent wire breakage of the cable, the trolley 10a and the trolley 10b are desirably anchored together with a fixture 18.

Configurations of Receiving Device and Antenna Cable

Incidentally, a healthcare personnel changes a posture of the subject 3 depending on what examination is to be made when capturing an in-vivo image by using a conventional capsule endoscope system. However, in conventional capsule endoscope systems, the receiving device 8 for receiving image data wirelessly transmitted from the capsule endoscope 4 is attached to a side surface of the body of the subject 3; accordingly, contact between the receiving device 8 and a bed or the like can occur when an attempt of posture change is made, making it difficult to change the posture of the subject 3 in some cases. To this end, in the capsule endoscope system according to an embodiment of the present invention, the antenna cable 7 and the receiving device 8 are configured as described below to thereby facilitate posture change of the subject 3. Configurations of the antenna cable 7 and the receiving device 8 according to first through third embodiments of the present invention are described below with reference to FIG. 4 through FIG. 6.

First Embodiment

Figure 4:
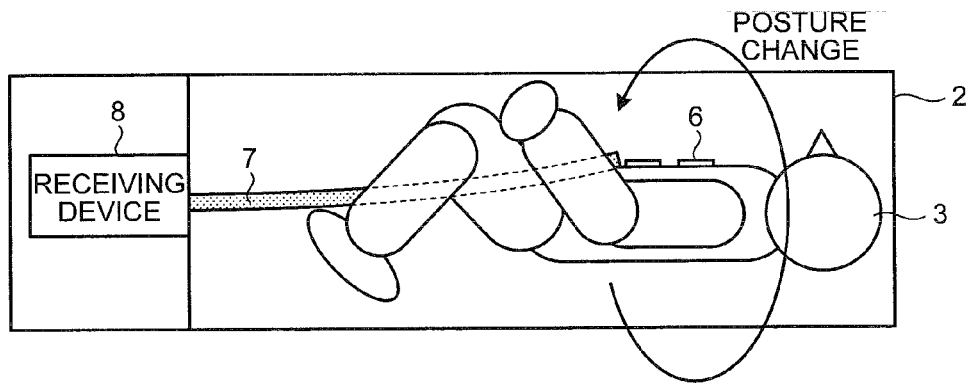
FIG. 4 is a schematic diagram illustrating configurations of an antenna cable and a receiving device according to a first embodiment of the present invention.

FIG. 4 is a schematic diagram illustrating the configurations of the antenna cable 7 and the receiving device 8 according to the first embodiment of the present invention. As illustrated in FIG. 4, in the present embodiment, the receiving device 8 is fixed to a longitudinal end portion of the bed 2, on which the subject 3 is to be placed. Hence, the receiving device 8 arranged in this manner allows the subject 3 to change the posture easily.

The antenna cable 7 is wired along a body axis of the subject 3. These configurations of the antenna cable 7 and the receiving device 8 cause the antenna cable 7 to be consistently located on the body axis of the subject 3, thereby facilitating posture change of the subject 3 while preventing wire breakage of the antenna cable and winding of the antenna cable around the subject, which can result from application of stress on two end portions of the antenna cable.

Second Embodiment

Figure 5:
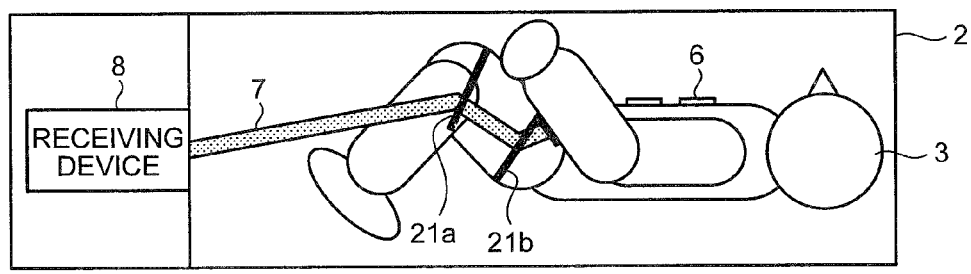
FIG. 5 is a schematic diagram illustrating configurations of an antenna cable and a receiving device according to a second embodiment of the present invention.

FIG. 5 is a schematic diagram illustrating the configurations of the antenna cable 7 and the receiving device 8 according to the second embodiment of the present invention. As illustrated in FIG. 5, in the present embodiment, the receiving device 8 is fixed to a longitudinal end portion of the bed 2, on which the subject 3 is to lie; the antenna cable 7 connecting the antenna 6 and the receiving device 8 together is fixed to the subject 3 at a neighborhood of knees and at a neighborhood of thighs with fixtures 21a and 21b, such as Velcro tape (registered trademark). These configurations of the antenna cable 7 and the receiving device 8 cause, when the subject 3 changes the posture, a portion of the antenna cable 7, the portion being between the neighborhood of the knees where the antenna cable 7 is fixed to the subject 3 and a connecting portion where the antenna cable 7 is connected to the receiving device 8, to rotate. However, the distance between the neighborhood of the knees where the antenna cable 7 is fixed to the subject 3 and the connecting portion where the antenna cable 7 is connected to the receiving device 8 is short as compared to a total length of the antenna cable 7; accordingly, posture change of the subject 3 can be facilitated while preventing wire breakage of the antenna cable 7 and winding of the antenna cable 7 around the subject 3. The antenna cable 7 can be fixed to the subject 3 at, in addition to the neighborhood of the knees and the neighborhood of the thighs, at a neighborhood of ankles.

Third Embodiment

Figure 6:
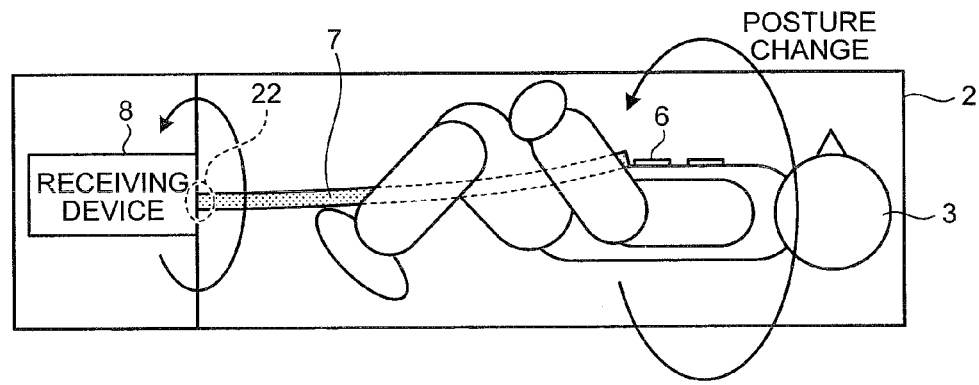
FIG. 6 is a schematic diagram illustrating configurations of an antenna cable and a receiving device according to a third embodiment of the present invention.

FIG. 6 is a schematic diagram illustrating the configuration of the antenna cable 7 and the receiving device 8 according to the third embodiment of the present invention. As illustrated in FIG. 6, in the present embodiment, the receiving device 8 is fixed to a longitudinal end portion of the bed 2, on which the subject 3 is to lie. A rotation mechanism 22 that allows the connecting portion, at which the antenna cable 7 is connected to the receiving device 8, to rotate about a rotation axis that lies in the longitudinal direction in response to posture change of the subject 3 is provided at the connecting portion, at which the antenna cable 7 is connected to the receiving device 8. Alternatively, a similar rotation mechanism 22 for causing the receiving device 8 itself to rotate in response to posture change of the subject 3 can be provided. These configurations of the antenna cable 7 and the receiving device 8 allow the connecting portion, at which the antenna cable 7 is connected to the receiving device 8, or the receiving device 8 itself to rotate in response to posture change of the subject 3, thereby facilitating posture change of the subject 3 while preventing wire breakage of the antenna cable 7 and winding of the antenna cable 7 around the subject 3, which can result from application of stress on the two end portions of the antenna cable 7.

Descriptions have been made of the embodiments, to which the invention made by the inventors of the present invention is applied; however, the present invention is not limited to the descriptions and the drawings, which form a part of the disclosure of the present invention according to the embodiments. For instance, in the embodiments, the receiving device 8 is fixed to the longitudinal end portion of the bed 2; however, the device fixed to the longitudinal end portion of the bed 2 is not limited to the receiving device 8. For instance, for a situation where the receiving device 8 is compact and will not prevent posture change of the subject 3, other information processing device, such as a display device that displays the image data output from the receiving device 8, can be fixed to the longitudinal end portion.

Figure 7:
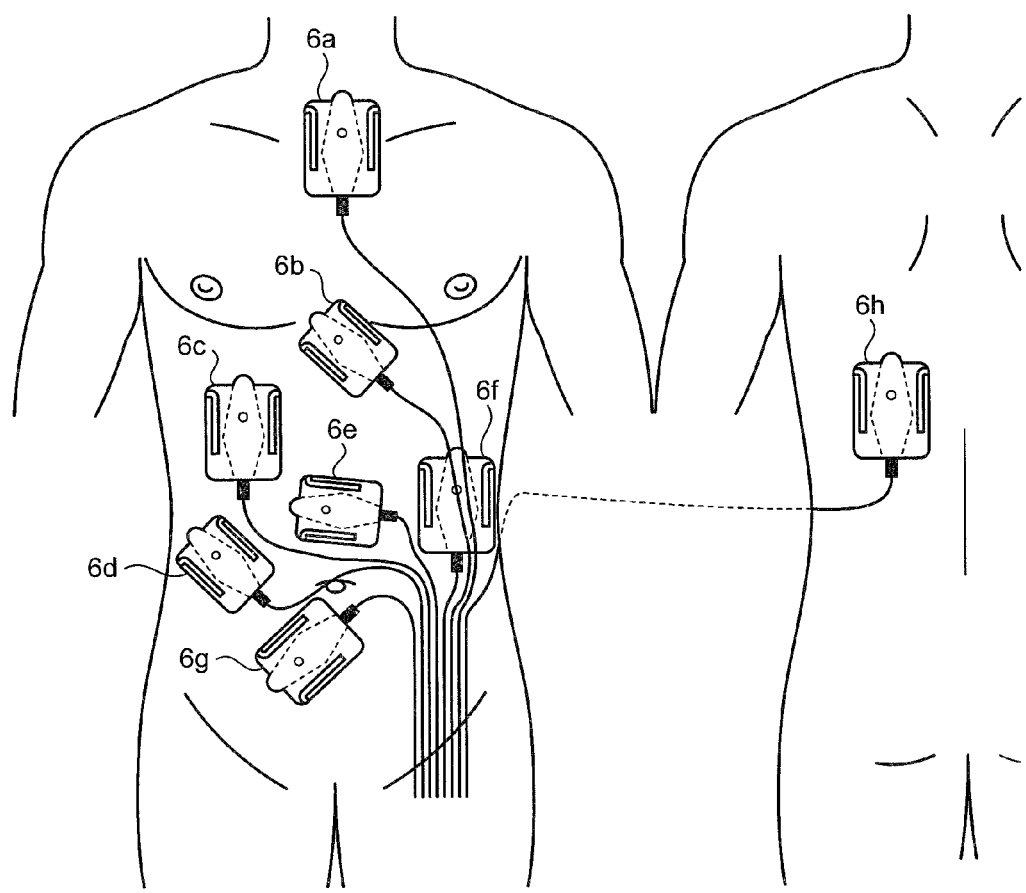
FIG. 7 is a diagram illustrating an optimum arrangement of antennas for observation of an esophagus or a stomach of a subject.

In the embodiments, no mention is made of location of the antenna 6 to be arranged onto the body surface of the subject 3; however, the location of the antenna 6 is desirably determined while taking a receivable area (directivity) of the antenna 6 into consideration. More specifically, when the esophagus or the stomach of the subject is to be observed, a plurality of antennas 6a to 6h are desirably arranged as illustrated in FIG. 7. In the arrangement illustrated in FIG. 7, the antenna 6a, the antenna 6b, the antenna 6c, the antenna 6d, the antenna 6e, the antenna 6f, the antenna 6h, and the antenna 6h, are attached to a subject at a position immediately above a manubrium portion, at a position immediately above a xiphisternum portion, at a position immediately above an eighth rib, at a position on the right of the umbilicus, at a position on the upper side of the umbilicus, at the upper left of the umbilicus, at a slightly rightward position relative to a center of the body and on the lower side of the umbilicus, and at a position on the eighth rib on the back of the subject, respectively.

The antenna 6g is arranged on the back to cover an area, in which the stomach is located, extending rearward from the surface of the abdomen. The antenna 6a for complementing the antenna 6b acquires images on a way moving from the esophagus to the cardia. Such an arrangement of the antennas 6 allows the number of the antennas 6 and the antenna cables 7 to be reduced to a minimum number; accordingly, the posture change of the subject 3 is facilitated and cost reduction can be achieved. Other embodiments, examples, application techniques, and the like, which can be made by those skilled in the art or the like based on the embodiments in such a manner as discussed above, are all incorporated in the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus system comprising:
a table for placing a subject thereon along a longitudinal direction, the table having a width portion and a length portion, the width portion being smaller in dimension than the length portion;
a capsule medical apparatus configured to be inserted into the subject;
an antenna for receiving in-vivo information transmitted from the capsule medical apparatus inserted into the subject, the antenna being configured to be arranged on a body surface of the subject;
a cable for transmitting the in-vivo information received by the antenna to a receiving device;
the receiving device for receiving the in-vivo information transmitted via the cable, the receiving device being fixed to the width portion of the table;
a rotatable connector connecting the cable to the receiving device; and
a rotation mechanism provided at the connector for rotating one of the receiving device or the connector about a rotation axis that lies in the longitudinal direction of the table depending on posture change of the subject.

2. The capsule medical apparatus system of claim 1, further comprising:
a display device for displaying the in-vivo information; and
a control device that includes a transfer unit for transferring the in-vivo information transmitted from the capsule medical apparatus to the display device.

3. The capsule medical apparatus system of claim 1, wherein the capsule medical apparatus is configured to acquire image information as the in-vivo information.

4. The capsule medical apparatus system of claim 1, further comprising a guidance magnetic-field generating device, wherein
the capsule medical apparatus includes at least one magnetic material, and
the guidance magnetic-field generating device acts on the magnetic material to guide the capsule medical apparatus.

* * * * *